US011013430B2

(12) United States Patent
Tanriover et al.

(10) Patent No.: US 11,013,430 B2
(45) Date of Patent: May 25, 2021

(54) METHODS AND APPARATUS FOR IDENTIFYING FOOD CHEWED AND/OR BEVERAGE DRANK

(71) Applicant: Intel Corporation, Santa Clara, CA (US)

(72) Inventors: Cagri Tanriover, Bethany, OR (US); Nese Alyuz Civitci, Hillsboro, OR (US); Asli Arslan Esme, Istanbul (TR); Hector Alfonso Cordourier Maruri, Guadalajara (MX); Paulo Lopez Meyer, Zapopan (MX)

(73) Assignee: Intel Coproration, Santa Clara, CA (US)

( * ) Notice: Subject to any disclaimer, the term of this patent is extended or adjusted under 35 U.S.C. 154(b) by 412 days.

(21) Appl. No.: 16/019,333

(22) Filed: Jun. 26, 2018

(65) Prior Publication Data
US 2019/0038186 A1 Feb. 7, 2019

(51) Int. Cl.
*A61B 5/11* (2006.01)
*A61B 5/00* (2006.01)
(Continued)

(52) U.S. Cl.
CPC .......... *A61B 5/1126* (2013.01); *A61B 5/4205* (2013.01); *A61B 5/4542* (2013.01); *A61B 5/6803* (2013.01); *A61B 5/7207* (2013.01); *A61B 5/7275* (2013.01); *G16H 20/60* (2018.01); *G16H 50/70* (2018.01); *A61B 5/113* (2013.01); *A61B 5/6819* (2013.01);
(Continued)

(58) Field of Classification Search
CPC ... A61B 5/4205; A61B 5/4542; A61B 5/6803; A61B 5/6819; A61B 5/7264; G16H 20/60
See application file for complete search history.

(56) References Cited

U.S. PATENT DOCUMENTS 4,520,238 A * 5/1985 Ikeda ...................... H04R 1/46
381/151
2016/0232811 A9 8/2016 Conner
(Continued)

OTHER PUBLICATIONS

Farooq, Segmentation and Characterization of Chewing Bouts by Monitoring Temporalis Muscle Using Smart Glasses With Piezoelectric Sensor, IEEE Journal of Biomedical and Health Informatics, vol. 21, No. 6, Nov. 2017 (Year: 2017).*
(Continued)

*Primary Examiner* — Michael J Dalbo
(74) *Attorney, Agent, or Firm* — Schwabe, Williamson & Wyatt, P.C.

(57) ABSTRACT

Methods and apparatuses for identifying food chewed or beverage drank are disclosed herein. In embodiments, a device may comprise one or more sensors to provide vibration signal data representative of vibrations sensed from a nasal bridge of a user wearing the device, a chewing analyzer to extract from the vibration signal data a first plurality of features associated with chewing activities, and/or a drinking analyzer is to extract from the vibration signal data a second plurality of features associated with drinking activities. The extracted first and/or second plurality of features, in turn, may be used to determine a category of food the user was chewing, or a category of beverage the user was drinking. In embodiments, the methods and apparatuses may use personalized models.

23 Claims, 9 Drawing Sheets

(51) Int. Cl.
  *G16H 20/60* (2018.01)
  *G16H 50/70* (2018.01)
  *A61B 5/113* (2006.01)
  *G09B 19/00* (2006.01)
(52) U.S. Cl.
  CPC .......... *A61B 5/7225* (2013.01); *A61B 5/7264* (2013.01); *G09B 19/0092* (2013.01)

(56) References Cited

U.S. PATENT DOCUMENTS

2017/0086779 A1* 3/2017 Kamano ................ A61B 7/04
2019/0038208 A1* 2/2019 Mohammadi .......... G16H 50/20

OTHER PUBLICATIONS

Alshuraf, Recognition of Nutrition Intake Using Time-Frequency Decomposition in a Wearable Necklace Using a Piezoelectric Sensor, IEEE Sensors Journal, vol. 15, No. 7, Jul. 2015 (Year: 2015).*

Kalantarian, Wearable Nutrition Monitoring System, 2014 11th International Conference on Wearable and Implantable Body Sensor Networks (Year: 2014).*

Sarrafzadeh, Monitoring eating habits using a piezoelectric sensor-based necklace, Computers in Biology and Medicine 58 (2015) 46-55 (Year: 2015).*

Haik Kalantarian et al., "A Wearable Nutrition Monitoring System", 2014, 6 pages, 11th International Conference on Wearable and Implantable Body Sensor Networks, University of California, Los Angeles, CA.

K. Suganya et al., "Recognition of Nutrition Intake using MEAS Piezoelectric Sensor", Oct. 2015, 7 pages, International Journal of Innovation Research in Advance Engineering (IJIRAE) ISSN: 2349-2163, Issue 10, vol. 2.

Muhammad Farooq et al., "A Novel Wearable Device for Food Intake and Physical Activity Recognition", Jul. 11, 2016, 13 pages, Tuscaloosa, AL.

Abdelkareem Bedri et al., "EarBit: Using Wearable Sensors to Detect Eating Episodes in Unconstrained Environments", Sep. 2017, 20 pages, Proceedings of the ACM on Interactive, Mobile, Wearable and Ubiquitous Technologies, vol. 1, No. 3, Article 37.

* cited by examiner

METHODS AND APPARATUS FOR IDENTIFYING FOOD CHEWED AND/OR BEVERAGE DRANK

FIELD OF THE DISCLOSURE

This disclosure relates generally to fields of computing, wearable devices, diet management, and, more particularly, in some embodiments, to wearable methods and apparatuses for identifying food chewed and/or beverage drank by a user.

BACKGROUND

Recognition of chewing and drinking activities during the day can provide a number of benefits such as the following:
1—Managing how fast a user chews and/drinks;
2—Indicate and/or predict how frequently a user eats within a day (i.e. too many or too few meals), or drinks within a week (e.g., how many soda and/or alcoholic drinks);
3—Indicate and/or predict how long a user spends on meals over a time window (e.g. per day, per week etc.);
4—Track medication intake (particularly useful for users who regularly have to take one or more medicines per day);
5—Indicate and/or predict whether a user is having too much or too little of a category of food and drink.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
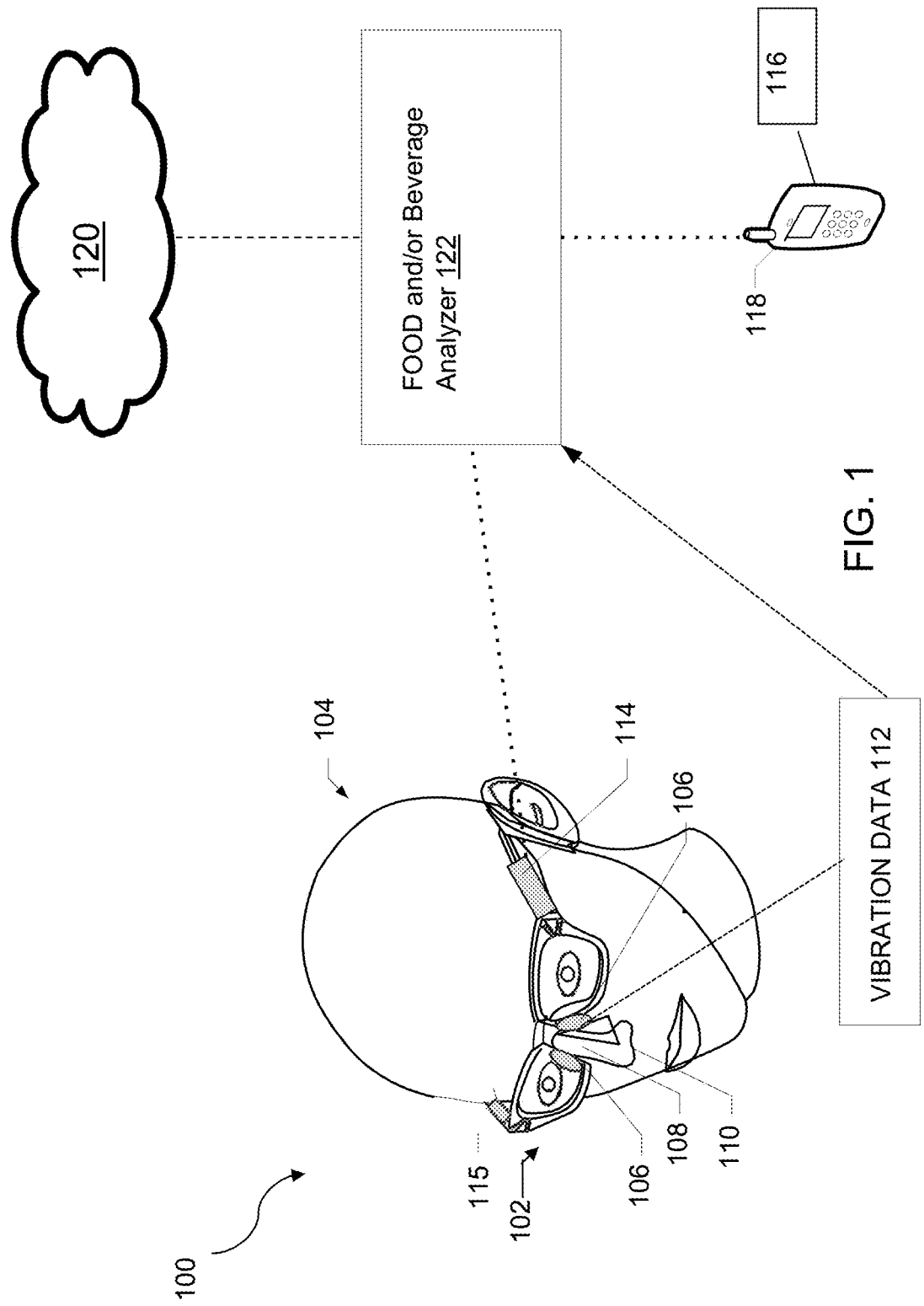
FIG. 1 illustrates an example system constructed in accordance with embodiments of the teaching disclosed herein, and including a food and/or beverage analyzer.

Methods and apparatuses for identifying food chewed or beverage drank are disclosed herein. In embodiments, a device, e.g., a wearable device, may comprise one or more sensors to provide vibration signal data representative of vibrations sensed from a nasal bridge of a user wearing the device, a chewing analyzer to extract from the vibration signal data a first plurality of features associated with chewing activities, and/or a drinking analyzer to extract from the vibration signal data a second plurality of features associated with drinking activities. The extracted first and/or second plurality of features, in turn, may be used to determine a category of food the user was chewing, or a category of beverage the user was drinking.

In embodiments, the device may further comprise at least a selected one of a food classifier or a beverage classifier. The food classifier may be coupled to the chewing analyzer to receive and process the extracted first plurality of features associated with chewing activities to determine the category of food the user was chewing. The beverage classifier may be coupled to the drinking analyzer to receive and process the extracted second plurality of features associated with drinking activities to determine the category of beverage the user was drinking.

In embodiments, at least one of the chewing analyzer, the drinking analyzer, the food classifier or the beverage classifier performs the extraction of the first plurality of features associated with chewing activities, the extraction of the second plurality of features associated with drinking activities, the determination of a category of food or the determination of a category of beverage, based at least in part on one or more personalized chewing and/or drinking models of the user.

In embodiments, the device may further comprise a breathing analyzer to receive and process the vibration signal data to determine whether the vibration signal data are representative of breathing of the user. The chewing analyzer may be coupled to the breathing analyzer, and perform the processing of the vibration signal data to attempt to extract from the vibration signal data the first plurality of features associated with chewing activities, based at least in part on determination that the vibration signal data are not representative of breathing of the user. The drinking analyzer may be coupled to the breathing analyzer, and perform the processing of the vibration signal data to attempt to extract from the vibration signal data the second plurality of features associated with drinking activities, based at least in part on determination that the vibration signal data are not representative of breathing of the user.

In embodiments, the device may further comprise an artifact analyzer to receive and process the vibration signal data to determine whether the vibration signal data are representative of one or more artifacts of the user. The chewing analyzer may be coupled to the artifact analyzer, and perform the processing of the vibration signal data to attempt to extract from the vibration signal data the first plurality of features associated with chewing activities, based at least in part on determination that the vibration signal data are not representative of one or more artifacts of the user. The drinking analyzer may be coupled to the artifact analyzer, and perform the processing of the vibration signal data to attempt to extract from the vibration signal data the second plurality of features associated with drinking activities, based at least in part on determination that the vibration signal data are not representative of one or more artifacts of the user.

In embodiment, the device may be an eyewear having a frame with a nose bridge and a plurality of bridge arms, and the one or more sensors are proximally disposed at the bridge arms.

In the description to follow, references are made to the accompanying drawings, which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Operations of various methods may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiments. Various additional operations may be performed and/or described operations may be omitted, split or combined in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous. The term "non-transitory computer readable medium" is expressly defined to include any type of computer readable storage device and/or storage disk and to exclude propagating signals and to exclude transmission media.

As used hereinafter, including the claims, the terms "interface" and "engine" may refer to, be part of, or include an Application Specific Integrated Circuit (ASIC), an electronic circuit, a programmable combinational logic circuit (e.g., field programmable gate arrays (FPGA)), a processor (shared or dedicate) and/or memory (shared or dedicated) that execute a plurality of programming instructions of one or more software or firmware programs to provide the described functionality.

FIG. 1 illustrates an example system 100 constructed in accordance with the teachings of this disclosure for identifying food chewed and/or beverage drank by a subject or user (the terms "user" and "subject" are used interchangeably herein and both refer to a biological creature such as a human being). In embodiments, the example system 100 may include a wearable device 102 to be worn by a user 104. In the example of FIG. 1, the wearable device 102 includes eyeglasses worn by the user 104. However, the wearable device 102 can include other wearables, such as, a helmet, a mask or a nasal strip.

The wearable device 102 may include one or more sensors 106. In the example of FIG. 1, the sensor(s) 106 may be piezoelectric sensor(s). The sensor(s) 106 may be positioned on the wearable device 102 such that when the user 104 wears the wearable device 102, the sensor(s) 106 are disposed proximate to a bridge 108 of a nose 110 of the user 104. For example, the sensor(s) 106 may be positioned at the bridge or nose pads of the bridge arms of the frame of the eyewear 102. As the user 104 inhales and exhales, chews food, drinks beverages, or otherwise moves his/her head (or parts thereof, like his/her eyes, ear, mouth/throat or nose), the sensor(s) 106 may detect vibrations of the nasal bridge 108. In particular, the piezoelectric sensor(s) 106 may deform and generate electrical signal data based on the vibrations of the nasal bridge 108 during these activities. The sensor(s) 106 may be configured to measure the nasal bridge vibrations for a period of time (e.g., whenever the user 104 is wearing the wearable device 102, for a specific duration (e.g., not always on when the user is wearing the device 102), etc.). In other examples, the sensor(s) 106 may measure vibrations at other portions of the user's body (e.g., the user's temples, the user's forehead). The wearable device 102 can include additional or fewer sensor(s) 106 than illustrated in FIG. 1. Also, the wearable device 102 can include other types of sensor(s) 106 and/or other means for generating the vibration data (e.g., via sound recordings). As used herein, vibration data is defined to include nasal bridge vibration data with or without other types of data such as sound data collected by other sensors.

The example system 100 of FIG. 1 may further include one or more semiconductor device with processor and storage to store vibration signal data (or simply, vibration data) 112 generated by the sensor(s) 106, process the vibration data 112 generated by the sensor(s) 106, and/or generate one or more outputs based on the processing of the vibration data. For example, as illustrated in FIG. 1, a processor 114 (with storage) may be coupled (e.g., mounted) to a side of the frame of the example eyewear 102. Also, the wearable device 102 of FIG. 1 may include a battery 115 to provide power to the processor 114 and/or other components of the wearable device 102. Further, the wearable device 102 of FIG. 1 may include an analog to digital (A/D) converter (not shown) to digitize the analog signals output by sensor(s) 106 for the processor 114 and/or other components of the wearable device 102. In embodiments, the A/D converter may be part of the processor 114.

In other examples, the processor may be separate from the wearable device 102. For example, wearable device 102 may be further configured with communication circuitry (not shown) to transmit the vibration data 112 to a processor 116 of a user device 118 such as a smartphone or another wearable (e.g., a smart watch). In other examples, the communication circuitry may transmit the vibration data 112 to a cloud-based device 120 (e.g., one or more servers, processor(s), and/or virtual machine(s)). The dotted lines extending from the food and/or beverage analyzer 122 in FIG. 1 demarcate the different locations for the food and/or beverage analyzer 122 (e.g., on the wearable 102, in the cloud 120, and/or in a wearable or non-wearable user device 118). Appropriate communication paths (e.g., via WiFi, cellular, Bluetooth, Near Field Communication (NFC)), and/or other communication protocols may be supported by the communication circuitry.

In some examples, the processor 114 of the wearable device 102 may be communicatively coupled to one or more other processors. In such examples, the sensor(s) 106 may transmit the vibration data 112 to the on-board processor 114 of the wearable device 102. The associated communication circuitry may in turn transmit the vibration data 112 to the processor 116 of the user device 118 and/or the cloud-based device 120. In some such examples, the wearable device 102 (e.g., the sensor(s) 106 and/or the on-board processor 114) and the processor(s) 116, 120 may be communicatively coupled via one or more wired connections (e.g., a cable) or wireless connections (e.g., cellular, Wi-Fi, NFC or Bluetooth connections).

In the example system 100 of FIG. 1, the vibration data 112 may be processed by a food and/or beverage analyzer 122. The example food and/or beverage analyzer 122 may be implemented by software respectively (or jointly) executed on the processor 114 of the wearable device 102, the processor 116 of the wearable or non-wearable user device 118, and/or the cloud-based device 120. In some examples, one or more components of the example food and/or beverage analyzer 122 may be implemented by the on-board processor 114 of the wearable device 102 and one or more other components may be implemented by the processor 116 of the user device 118 and/or the cloud-based device 120.

In the example system 100 of FIG. 1, the food and/or beverage analyzer 122 may serve to process the vibration data generated by the sensor(s) 106 to identify chewing and/or drinking activities, and in turn, food chewed and/or beverages drank of the user 104. In the example system 100, the sensor(s) 106 may collect the vibration data 112 as the user 104 breathes, chews foods, drinks beverages or otherwise move his/her head (or parts thereof, such as the eyes, the ears, the mouth/throat, the nose, and so forth). The food and/or beverage analyzer 122 may receive and process the nasal bridge vibration data 112 generated by the sensor(s) 106. In some examples, the food and/or beverage analyzer 122 may receive the nasal bridge vibration data 112 in substantially real-time (e.g., near the time the data is collected). In other examples, the food and/or beverage analyzer 122 may receive the nasal bridge vibration data 112 at a later time (e.g., periodically and/or aperiodically) based on one or more settings but sometime after the chewing and/or drinking has occurred (e.g., seconds, minutes, hours, days, etc. later). The food and/or beverage analyzer 122 may perform one or more operations on the vibration data such as filtering the raw signal data, removing noise from the signal data, and/or analyzing the data. The food and/or beverage analyzer 122 may perform the operations at the on-board processor 114 and/or on one or more off-board processors, such as the processor 116 of the user device 124 and/or the cloud-based device 120.

The example food and/or beverage analyzer 122 may analyze the vibration data from the user 104 to extract features associated with chewing food and/or drinking beverages, and in turn, use the features to identify categories of food chewed and/or beverages drank. In embodiments, the example food and/or beverage analyzer 122 may analyze the vibration data 112 from the user 104 to determine breathing of the user, and analyze the vibration data 112 for food chewed and/or beverages drank during the non-breathing data intervals. In still other embodiments, the example food and/or beverage analyzer 122 may analyze the vibration data 112 from the user 104 to determine artifacts, and remove the artifacts from the vibration data 112, prior to analyzing the vibration data 112 for breathing, food chewed and/or beverages drank. These and other aspects will be described more fully below, with references to the remaining figures.

In some examples, the food and/or beverage analyzer 122 may generate one or more outputs based on the user's food chewing and/or beverage drinking activities. The outputs can, for example, be used to monitor the user's eating and/or drinking, and be accumulated to determine the user's eating and/or drinking habits. The determined eating and/or drinking habits can be used in turn to make recommendations for the user to adjust his or her eating and/or drinking habits to provide e.g., for a more healthy lifestyle. The output, including the accumulated data and recommendations can be presented via various devices of the user, including, but is not limited to smartphone 118.

Figure 2:
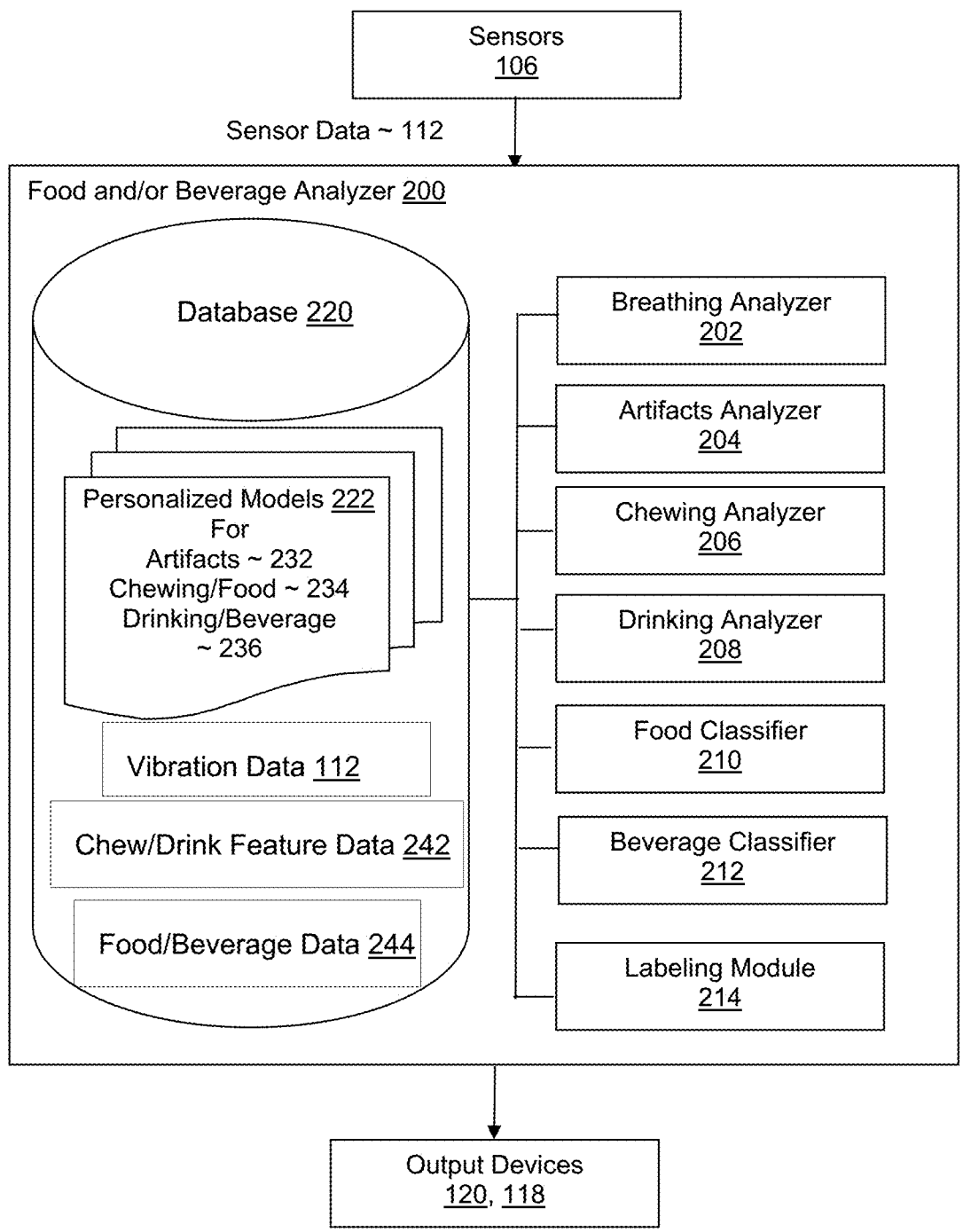
FIG. 2 is a block diagram of an example implementation of the food and/or beverage analyzer of FIG. 1, according to various embodiments.

FIG. 2 is a block diagram of an example implementation of the example food and/or beverage analyzer 200, which may be food and/or beverage analyzer 122 of FIG. 1. As mentioned above, the example food and/or beverage analyzer 200 may be constructed to identify chewing and/or drinking activities of a user (e.g., the user 104 of FIG. 1) and in turn, the food chewed and/or beverages drank. In the example of FIG. 2, the food and/or beverage analyzer 200 may be implemented by one or more of the processor 114 of the wearable device 102 of FIG. 1, the processor 116 of the user device 118, and/or cloud-based devices 120 (e.g., the server(s), processor(s), and/or virtual machine(s) 120 of FIG. 1). In some examples, some of the chewing and/or drinking analysis may be implemented by the food and/or beverage analyzer 200 via a cloud-computing environment and one or more other parts of the analysis may be implemented by the processor 114 of the wearable device 102 and/or the processor 116 of the user device 118.

In some examples, the location(s) at which the analysis is performed by the food and/or beverage analyzer 200 may be based on whether the analysis is to be performed in substantially real-time as the vibration data 112 is being generated or whether the analysis is to be performed at a later time. For example, if the analysis is to be performed in substantially real-time as the vibration data 112 is being generated, the analysis may be performed at the processor 114 of the wearable device 102. In other examples, if the analysis is to be performed at a later time and/or if the vibration data 112 is to be transferred to the food and/or beverage analyzer 200 at a later time, then the analysis may be performed at the processor 116 of the user device 118 or of one or more servers in cloud 120.

For the illustrated embodiments, the food and/or beverage analyzer 200 of FIG. 2 may receive sensor data 112 from sensors 106 (after they've been converted and digitized, if necessary). The analysis and identification results may be outputted to any one of a number of output devices, which may be device 118 or devices in cloud 120 of FIG. 1. In embodiments, the food and/or beverage analyzer 200 of FIG. 2 may include a database 220. In other examples, the database 220 may be located external to the food and/or beverage analyzer 200 in a location accessible to the analyzer, e.g., on user device 118 or on a server in cloud 120. As disclosed above, the vibration data 112 generated by the sensor(s) 106 as the user 104 breathes, chews, drinks or otherwise moves part of his/her head, after digitization, if necessary, may be transmitted to the food and/or beverage analyzer 200. In the illustrated example, the database 220 may provide means, such as persistent non-volatile storage, for storing the vibration data 112. In some examples, the database 220 may also provide means, such as persistent non-volatile storage, for storing the chewing and/or drinking feature data 242 extracted from vibration data 112. In still other examples, the database 220 may also provide means, such as persistent non-volatile storage, for storing the food and/or beverage data 244 identified using the extracted chewing and/or drinking feature data 242. The food and/or beverage data 244 may also include food and/or beverage recommendations provided to the user, based on the accumulated data.

In embodiments, database 220 may also include one or more personalized food and/or beverage models 222 of a user, used by the food and/or beverage analyzer 200 to assist in the extraction the chewing and/or drinking related features from vibration data 112, as well as to assist in the identification of the food chewed and/or beverage drank using the extracted chewing and/or drinking related feature data 242. As shown, for the illustrated embodiments, the personalized food and/or beverage models 222 may include artifact signal profiles 232, chewing and food signal profiles 234, and drinking and beverage signal profiles 236.

Figure 5A:
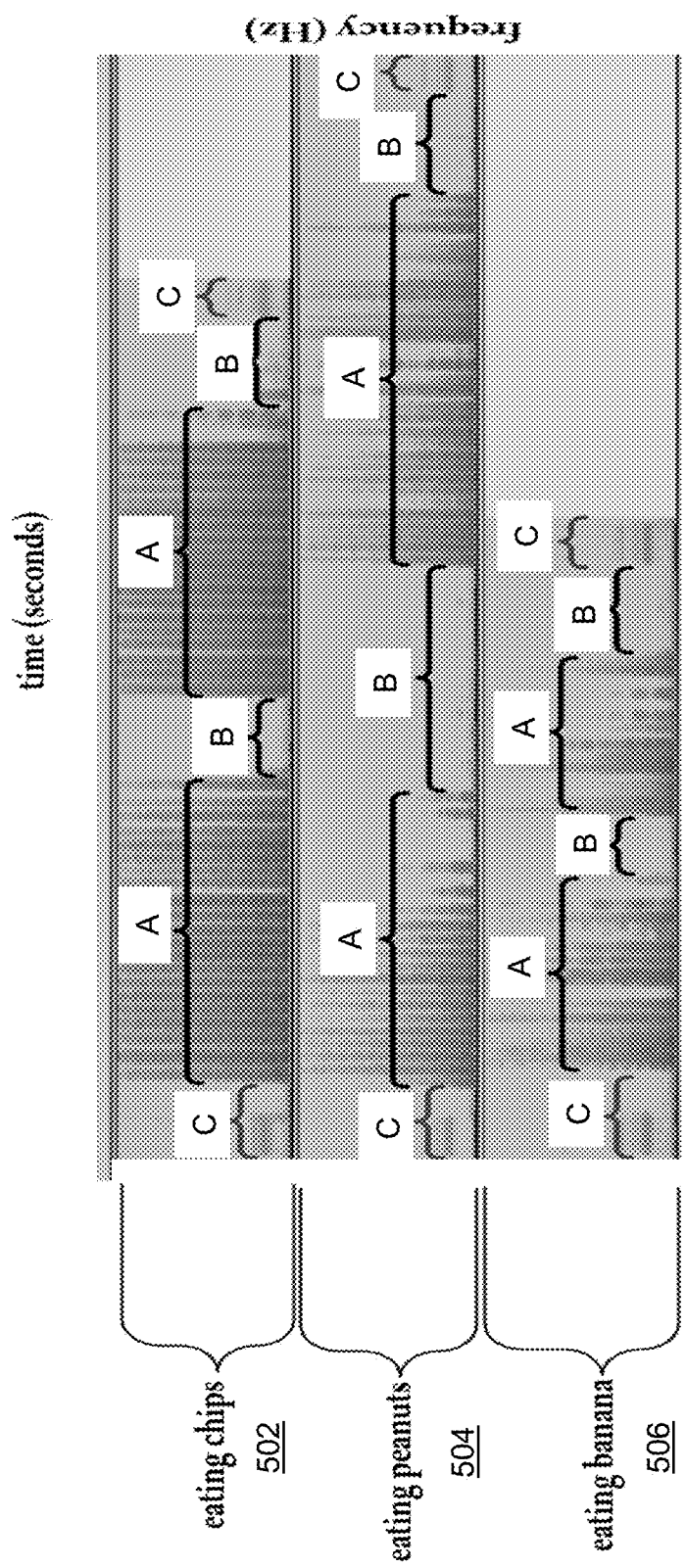
FIG. 5A-5D are example graphs illustrating signal patterns for various food chewed, various beverages drank, and artifacts, according to various embodiments.

Referring now to FIG. 5A-5D, wherein various example chewing and food signal profiles, drinking and beverage signal profiles, and artifact signal profiles are shown. In particular, FIG. 5A shows three (3) example chewing and food signal profiles, chewing and food signal profile 502 for eating chip, chewing and food signal profile 504 for eating peanuts, and chewing and food signal profile 506 for eating banana. As can be seen from these example profiles 502-506, different food chewing activities exhibit different vibration profiles (in terms of vibration frequencies (Y-axis) over different time period windows (X-axis), as well as amplitudes/intensity/energy of the vibrations (denoted by the darkness of the portions of the graphs)). The "A" time period windows in each of these example profiles 502-506 show the corresponding vibration frequencies while chewing the particular type of food (chips, peanuts, and banana). The "B" time period windows in each of these example profiles 502-506 show the corresponding vibration frequencies while the particular type of chewed food (chips, peanuts, and banana) was being swallowed. The "C" time period windows in each of these example profiles 502-506 show the starting and ending time of the collection of these example profiles.

Figure 5B:
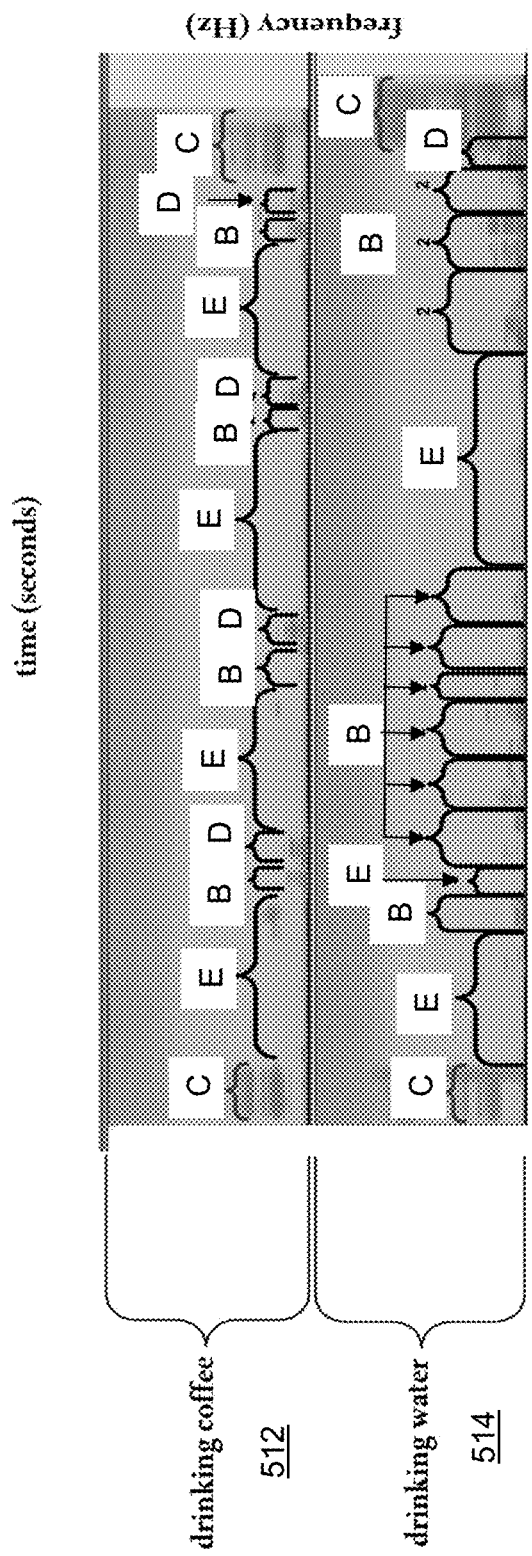

FIG. 5B shows two (2) example drinking and beverage signal profiles, drinking and beverage profile 512 for drinking coffee, and drinking and beverage signal profile 514 for drinking water. As can be seen from these example drinking and beverage signal profiles 512-514, similar to the chewing and food signal profiles 502-506, different beverage drinking activities exhibit different vibration profiles (in terms of vibration frequencies (Y-axis) over different time period windows (X-axis), as well as amplitudes/intensity/energy of the vibrations (denoted by the darkness of the portions of the graphs). As before, the "B" time period windows in each of these example profiles 512-514 show the corresponding vibration frequencies while the particular type of beverage (coffee and water) was being swallowed. The "C" time period windows in each of these example profiles 512-514 show the starting and ending time of the collection of these example profiles. The "D" time period windows in each of these example profiles 512-514 show the corresponding vibration frequencies while the user was exhaling in between swallowing of the particular type of beverage. The "E" time period windows in each of these example profiles 512-514 show the corresponding vibration frequencies while the user was breathing in between swallowing of the particular type of beverage.

Figure 5C:
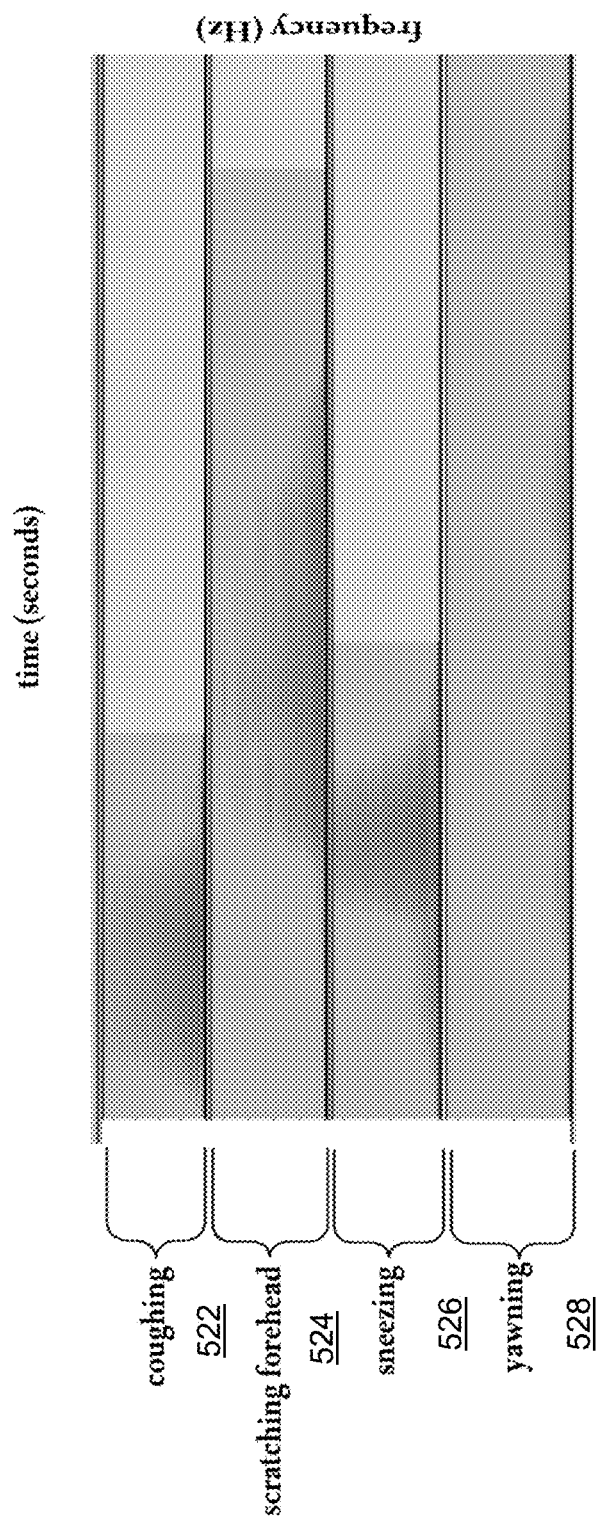

FIG. 5C shows four (4) example artifact signal profiles, artifact signal profile 522 for coughing, artifact signal profile 524 for scratching forehead, artifact signal profile 526 for sneezing, and artifact signal profile 528 for yawning. As can be seen from these example artifact profiles 522-528, similar to the chewing and food signal profiles 502-506 and drinking and beverage signal profiles 512-514, different artifacts exhibit different vibration profiles (in terms of vibration frequencies (Y-axis) over different time period windows (X-axis), as well as amplitudes/intensity/energy of the vibrations (denoted by the darkness of the portions of the graphs)).

Figure 5D:
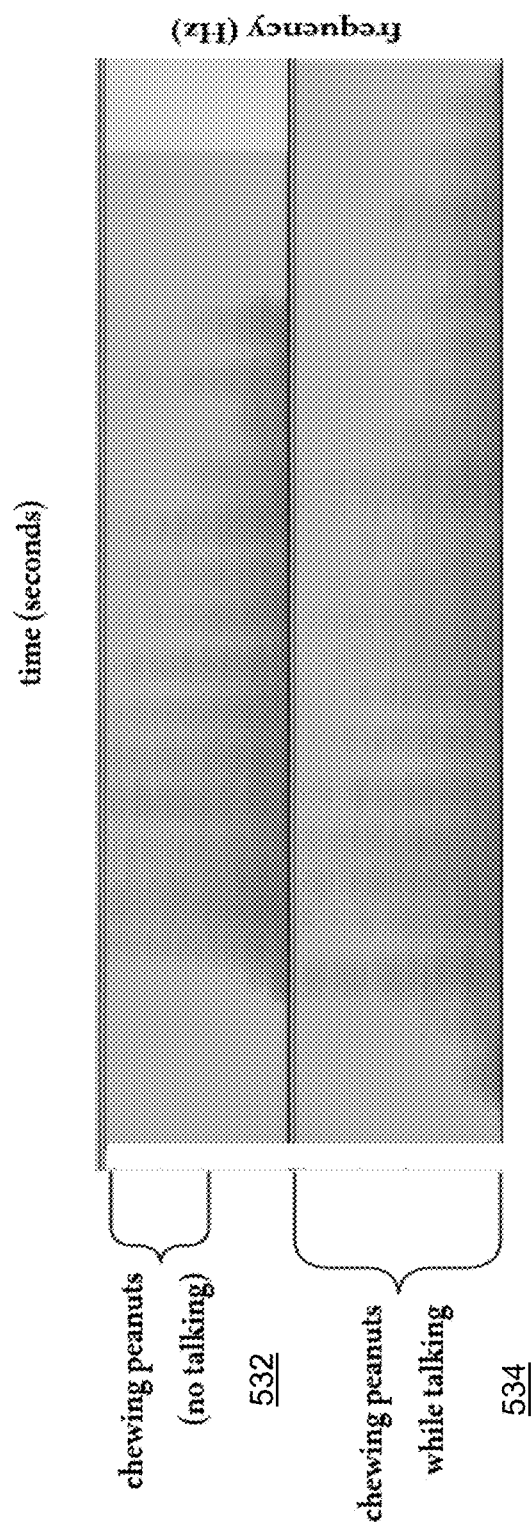

FIG. 5D shows an example comparison of a chewing and food signal profile without artifact, with a composite chewing and food signal profile with artifact, chewing peanuts signal profile 532 without talking, and chewing peanuts signal profile 534 while talking. As can be seen from the example comparison, different vibration profiles (in terms of vibration frequencies (Y-axis) over different time period windows (X-axis) as well as amplitudes/intensity/energy of the vibrations (denoted by the darkness of the portions of the graphs) may be exhibited when combined with an artifact. Thus, in implementations, depending on the accuracy desired, in addition to collecting multitudes of chewing and food signal profiles, drinking and beverage signal profiles and artifact signal profiles individually, composite profiles with artifacts may also be collected and employed.

As described earlier, in each of these Figures, FIG. 5A-5D, the "lightness/darkness" of the different frequency portions of the signal profiles, at particular points in time, represent the amplitudes of signals at the various frequencies at the particular points in time, i.e., the amount of energy present at the various frequencies at the particular points in time. The lighter an area represents the lower amount of amplitude or energy present, whereas the darker an area represents the higher amount of amplitude or energy present. Note that not only the amounts of energy vary for different chewing/drinking signal profiles, the frequencies at which the lower or higher energy are detected also vary for different chewing/drinking signal profiles.

In embodiments, in processing the vibration data, Fast Fourier Transform (FFT) may first be performed on the vibration data, with remainders of the processing performed using the outputs of the FFT calculations, with adjustable time and frequency resolutions. Employments of adjustable time and the frequency windows provide increased flexibility in the calculation of the energy levels.

Before further describing the present disclosure, it should be noted that for the artifact signal profiles, many of these artifacts are short time events compared to a typical chewing and drinking action. Therefore, such artifacts are only likely to affect a small portion of chewing and drinking signals. Additionally, except "scratching forehead" action, a human subject cannot be simultaneously engaged in chewing or drinking in any of the other actions (e.g. a person cannot be eating/drinking while coughing, yawning or sneezing). Therefore, many of these artifacts can be discriminated from chewing/drinking signals in time domain. Further, most energy of these artifacts (indicated by the "darkest" portions of the signal profiles in FIG. 5C) is present in the low frequency bands (i.e. sub 5 kHz band). Because the significant portion of chewing vibration energy is in the higher frequency bands (see FIG. 5A), even in the presence of such artifacts, the system (using the personalized models) has been observed to perform classification with acceptable accuracies. Impact of these artifacts is likely to be observed only on the portion of the weaker drinking signals that fall under the 5 kHz range.

Although most of the artifacts are unlikely to have a detrimental effect on the accurate detection of chewing signals, there is one artifact that might deserve special attention—talking while chewing. FIG. 5D provides a visualization of how such data appears. It can be seen that in the presence of speech, the energy level shifts towards the lower frequency bands. However, the energy bursts on the higher frequencies (due to periodic chewing action) is still clearly discernible in the data. Therefore, in experiments, it has been observed that the present system is able to cope with human speech artifacts observed during chewing. Obviously, human speech artifact is not likely to affect drinking signal profiles since it is virtually impossible to talk while drinking a beverage at the same time.

Referring back to FIG. 2, in addition to database 220, for the illustrated embodiments, food and/or beverage analyzer 200 may further include breathing analyzer 202, artifact analyzer 204, chewing analyzer 206, drinking analyzer 208, food classifier 210, beverage classifier 212, and labeling module 214, at least communicatively coupled to each other and database 220 as shown. Breathing analyzer 202 may be configured to identify breathing patterns of a user. Further details of breathing analyzer 202 may be found in U.S. patent application Ser. No. 15/669,137, titled METHODS AND APPARATUS FOR IDENTIFYING BREATHING PATTERNS, and filed on Aug. 4, 2017. Artifact analyzer 204, chewing analyzer 206, and drinking analyzer 208 may be configured to extract various signal features associated various artifacts, chewing of various foods, and drinking of various beverages respectively, from vibration data 112. Food classifier 210 and beverage classifier 212 may be configured to identify the food chewed and beverages drank, respectively, based on the extracted chewing/food feature data 242 and drinking/beverage feature data 244, respectively. Labeling module 214 may be configured to facilitate a user in labeling various artifact profiles 232, chewing/food profiles 234 and drinking/beverage profiles 236, when training food and/or beverage analyzer 200.

In embodiments, to attempt to extract from the vibration signal data a plurality of features associated with chewing activities, chewing analyzer 206 may be configured to analyze the vibration data for at least the following features:

Chewing feature 1—an average amount of energy present between a frequency band of about 0-22 kHz over a time period, Chewing feature 2—a duration ratio of a first duration of a first time period with energy above an energy threshold, and a second duration of a second time period, immediately following the first time period, with energy below the energy threshold, Chewing feature 3—a number of energy peaks above a frequency threshold between two time periods with energy below an energy threshold, and/or Chewing feature 4—a weighted average frequency for a time period.

Chewing feature 1—an average amount of energy present between a frequency band of about 0-22 kHz over a time period (window): In experiment, it has been observed that this feature may be a strong indicator of whether the chewing is taking place or not. While the time period/window width and the amount of energy detected during chewing is likely to vary from one subject to another, the width of the frequency band where presence of energy is most salient is likely to change depending on the type of food eaten.

Chewing feature 2—a duration ratio of a first duration of a first time period with energy above an energy threshold, and a second duration of a second time period, immediately following the first time period, with energy below the energy threshold: In experiment, it has been observed that the larger this ratio is, the faster the subject is eating since there will be a very short time gap between two successive chewing events. By keeping track of this information over time, prediction on the 'type' of food can also be made by cross comparing the ratios with the baseline chewing trend of the subject.

Chewing feature 3—a number energy peaks above a frequency threshold between two time periods with energy below an energy threshold: In experiment, it has been observed this feature indicates how many times a subject is actually chewing food before swallowing. As indicated in FIG. 5A-5D, the frequency and the number of energy peak occurrence will depend on the type of food chewed. For example, in the case of eating chips, between the start of the chewing event (the first "C" period), and the first swallowing event (the first "B" period), the subject has chewed about 21 times. The same subject has chewed the banana about 13 times, which is less and is expected given the softer texture of banana compared to chips.

Chewing feature 4—a weighted average frequency for a time period: In experiment, it has been observed that this feature provides a measure of where most of the energy is aggregated within the 0 to 22 kHz audible band. The significance of this feature is it provides information on the texture of the consumed food. As indicated in FIG. 5A-5D, while chewing soft textured food (such as banana) generates energy in the lower frequency bands, chewing crispy food (such as chips) tends to inject more energy towards the higher frequencies. Chewing peanuts, which are hard and dense, falls somewhere in between the former two.

In embodiments, to attempt to extract from the vibration data a plurality of features associated with drinking activities, the drinking analyzer may be configured to analyze the vibration data for Drinking feature 1—a size of a duration between two successive energy burst below about 5 kHz, Drinking feature 2—an integrated amount of energy over a time period, and/or Drinking feature 3—a number of swallowing incidents.

Drinking feature 1—a size of a duration between two successive energy burst below about 5 kHz: In experiment, it has been observed that this feature can be useful for differentiating between drinking an aromatic beverage (such as coffee) versus water. Each sip of coffee is followed by an exhalation event, which clearly indicates that the subject is inhaling (i.e. smelling to enjoy the aroma of the beverage) while sipping the coffee. There is no such inhalation indication while drinking water.

Drinking feature 2—an integrated amount of energy over a time period: In experiment, it has been observed that this feature can be useful in discriminating the type of drink the subject is having. According to data in FIG. 5B, the integration result of drinking water capture is expected to be greater than that of drinking coffee. The time window width can be chosen as a function of duration for event 'E' annotated on the spectrogram for drinking coffee (since the subject has long pauses between sips while drinking coffee where captured energy level is quite low).

Drinking feature 3—a number of swallowing incidents: Although drinking events inherently generate low energy vibrations on the nasal bone (see FIG. 5B), in experiment, it has been observed that based on statistical data on human behavior, presence of drinking action can be predicted indirectly. For example, while drinking cold drinks, people tend to swallow twice as frequently as when they perform swallowing for the purpose of throat clearing when drinking nothing.

Before further describing the present disclosure, it should be noted that in addition to the chewing and drinking features described, additional features (including, but are not limited to, standard deviation, average energy over different time windows and/or frequency bands etc.) can also be used as input to identifying food chewed and/or beverage drank. In particular, the additional features may be used during the training period. When it is possible to define features based on human observation and intuition, machine learning models may perform even better. In many cases even when features are defined in the absence of such observations on the available data, machine learning can still pick out hidden trends and categories. Therefore, by expanding the feature set in non-obvious ways, the power of machine learning may be leveraged to improve the accuracy of the food and/or beverage identification system.

While an example manner of implementing the example food and/or beverage analyzer 122/200 is illustrated in FIGS. 1 and 2, one or more of the elements, processes and/or devices illustrated in FIGS. 1 and 2 may be combined, divided, re-arranged, omitted, eliminated and/or implemented in any other way. Further, the example database 200, the example analyzers 202-208, the example classifiers 210-212, the example labeling module 214, and/or, more generally, the example food and/or beverage analyzer 122/200 of FIGS. 1 and 2 may be implemented by hardware, software, firmware and/or any combination of hardware, software and/or firmware. Thus, for example, any of the example database 200, the example analyzers 202-208, the example classifiers 210-212, the example labeling module 214, and/or, more generally, the example food and/or beverage analyzer 122/200 of FIGS. 1 and 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example database 200, the example analyzers 202-208, the example classifiers 210-212, the example labeling module 214, and/or, more generally, the example food and/or beverage analyzer 122/200 of FIGS. 1 and 2 is/are hereby expressly defined to include a non-transitory computer readable storage device or storage disk such as a memory, a digital versatile disk (DVD), a compact disk (CD), a Blu-ray disk, etc. including the software and/or firmware. Further still, the example food and/or beverage analyzer 122/200 of FIGS. 1 and 2 may include one or more elements, processes and/or devices in addition to, or instead of, those illustrated in FIGS. 1 and 2, and/or may include more than one of any or all of the illustrated elements, processes and devices.

Figure 3:
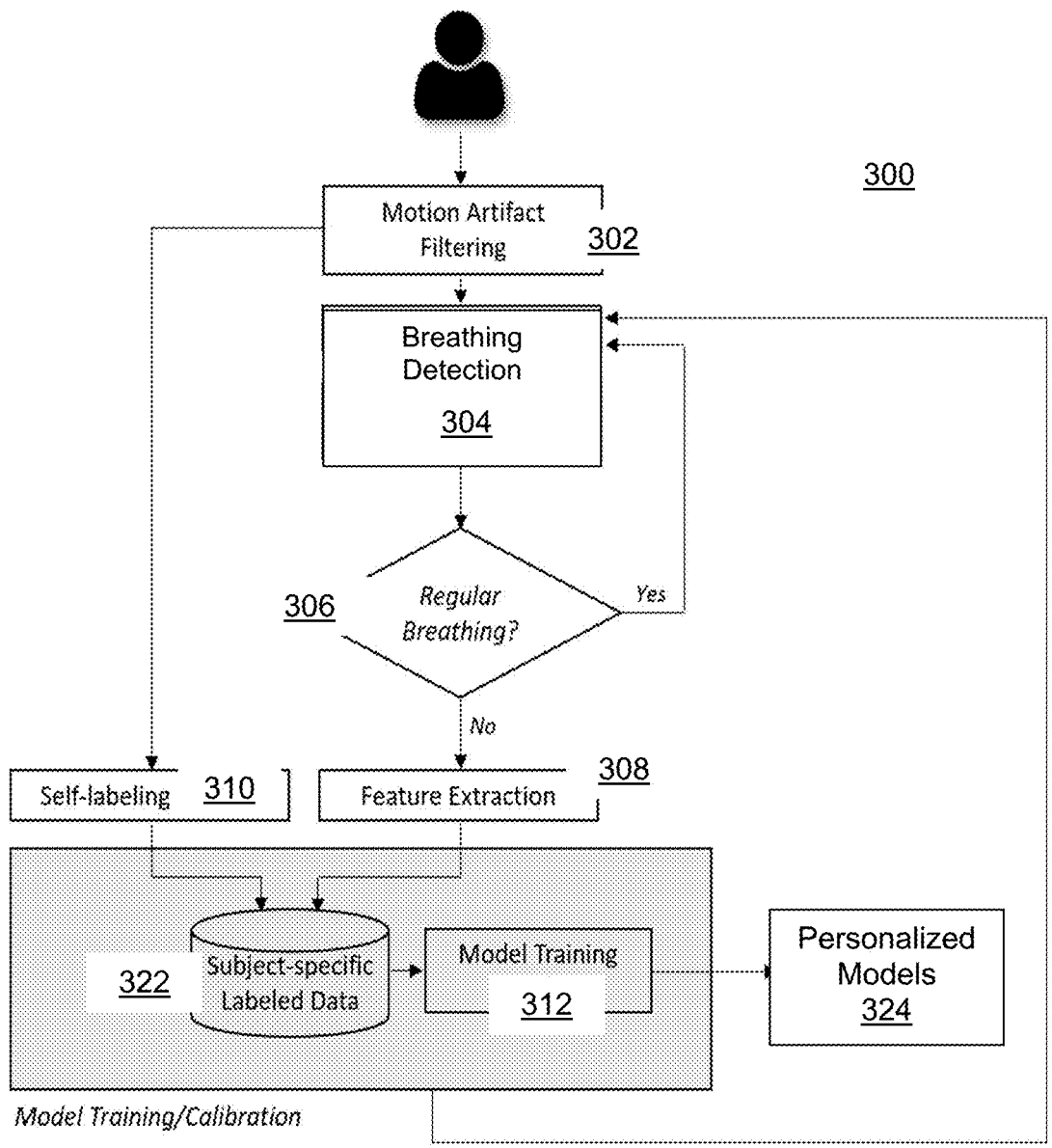
FIG. 3 is an example process for creating personalized models of a user, for identifying food chewed and/or beverages drank, according to various embodiments.

Referring now to FIG. 3, wherein an example process for creating personalized models of a user, for identifying food chewed and/or beverages drank, according to various embodiments, is shown. For the illustrated embodiments, process 300 for creating personalized models of a user, for identifying food chewed and/or beverages drank, may include operations performed at blocks 302-312. The operations may be performed e.g., by food and/or beverage analyzer 112/200 of FIG. 1-2.

As shown, process 300 may start at block 302. At block 302, the vibration signal data may be analyzed to identify artifacts, and have the motion artifacts filtered from the vibration signal data. Next, at block 304, on filtering the artifacts from the vibration signal data, the vibration signal data may be analyzed to identify breathing patterns of the user. In embodiments, breathing patterns may be identified using the techniques described in the above mentioned U.S. patent application Ser. No. 15/669,137. At block 306, a determination may be made on whether breathing patterns of the user was identified. If a result of the determination is affirmative, process 300 may continue to loop at block 304 until a result of the determination is negative, i.e., the vibration signal data do not represent breathing by the user.

On determination that vibration signal data do not represent breathing by the user, process 300 may proceed from block 306 to block 308. At block 308, attempts may be made to extract various food/chewing and/or beverage/drinking related features from the vibration signal data. The extracted food/chewing and/or beverage/drinking related features may be stored in data repository 322, which may be database 220 of FIG. 2.

In parallel with the vibration signal data analysis and feature extractions, at block 310, user specific labels may be inputted to label the food/chewing and/or beverage/drinking profiles being generated.

In embodiments, on accumulation of various food chewing and/or beverage drinking feature data, a machine learning process 312 may be operated to identify additional potential relevant features that might assist in identifying food chewed and/or beverages drank by the user.

On training, the resulting food chewing and/or beverage drinking features may be combined to form the personalized models 324 of the user, that may be used to identify food chewed and/or beverages drank by the user.

Figure 4:
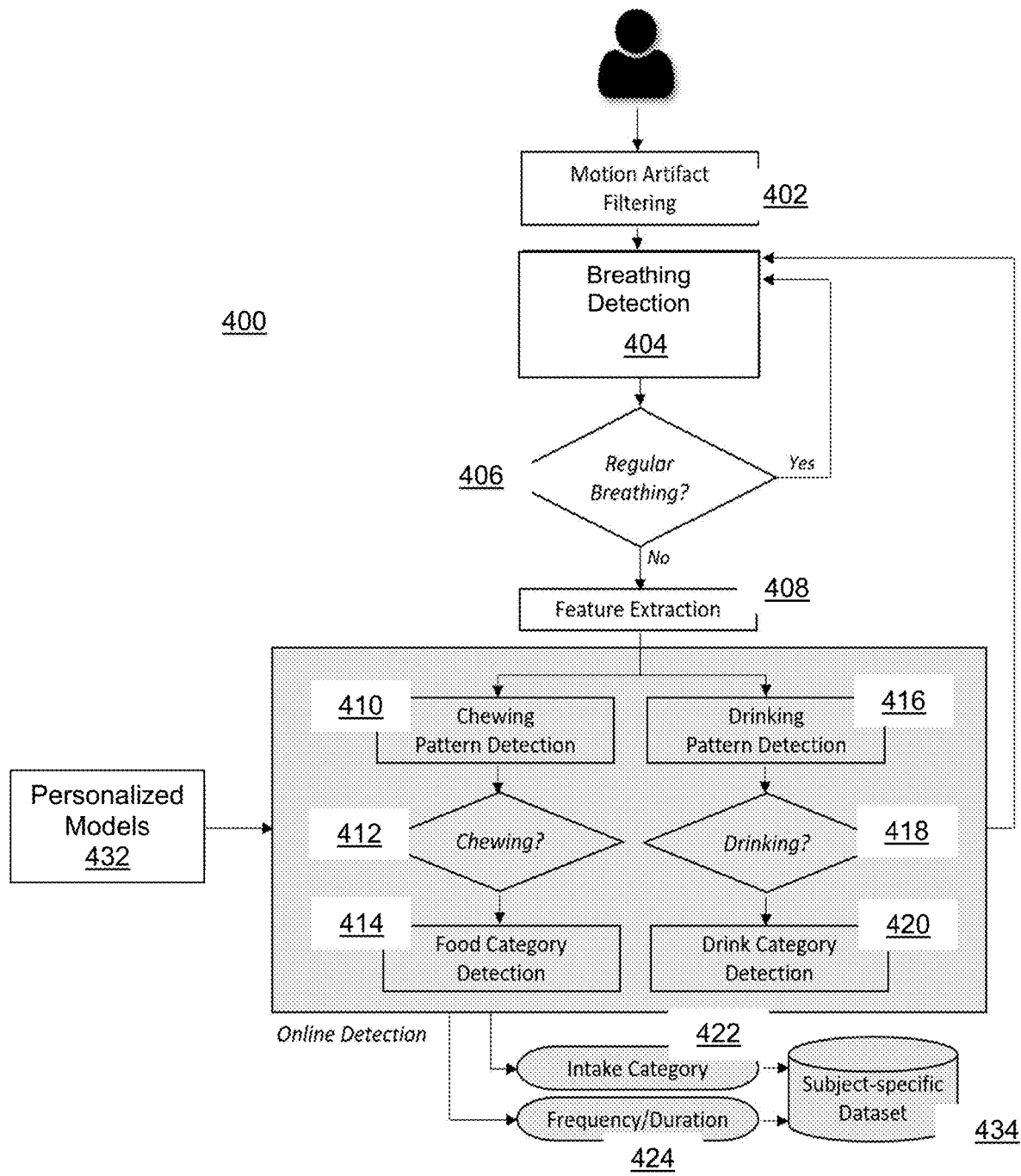
FIG. 4 is an example process for identifying food chewed and/or beverages drank, according to various embodiments.

Referring now to FIG. 4, wherein an example process for identifying food chewed and/or beverages drank, according to various embodiments, is shown. For the illustrated embodiments, process 400 for identifying food chewed and/or beverages drank, may include operations performed at blocks 402-424. The operations may be performed e.g., by food and/or beverage analyzer 112/200 of FIG. 1-2.

As shown, process 400 may start at block 402. At block 402, the vibration signal data may be analyzed to identify artifacts, and have the motion artifacts filtered from the vibration signal data. Next, at block 404, on filtering the artifacts from the vibration signal data, the vibration signal data may be analyzed to identify breathing patterns of the user. In embodiments, breathing patterns may be identified using the techniques described in the above mentioned U.S. patent application Ser. No. 15/669,137. At block 406, a determination may be made on whether breathing patterns of the user was identified. If a result of the determination is affirmative, process 400 may continue to loop at block 404 until a result of the determination is negative, i.e., the vibration signal data do not represent breathing by the user.

On determination that vibration signal data do not represent breathing by the user, process 400 may proceed from block 406 to block 408. At block 408, attempts may be made to extract various food/chewing and/or beverage/drinking related features from the vibration signal data.

From block 408, process 400 may proceed to block 410, and blocks 412 and 414 thereafter, or proceed to block 416, and blocks 418 and 420 thereafter. At block 410, the extracted features may be analyzed, using personalized (food/chewing and/or beverage/drinking) models 432, to identify chewing patterns. Then, at block 412, a determination may be made on whether chewing patterns has been detected. If chewing patterns have not been identified, the chewing analysis may terminate. If chewing patterns have been identified, at block 414, a category of the food chewed may be identified, using personalized (food/chewing and/or beverage/drinking) models 432.

Similarly, at block 416, the extracted features may be analyzed, using personalized (food/chewing and/or beverage/drinking) models 432 to identify drinking patterns. Then, at block 418, a determination may be made on whether drinking patterns has been detected. If drinking patterns have not been identified, the drinking analysis may terminate. If drinking patterns have been identified, at block 420, a category of the beverage drank may be identified, using personalized (food/chewing and/or beverage/drinking) models 432.

In embodiments, on accumulation of various food chewing and/or beverage drinking feature data, various food and beverage consumption analyses may be performed at blocks 422 and 424. For example, the accumulated data may be analyzed to determine the category of food the user has consumed over a particular time period. The results of the analysis may indicate whether the user is consuming the right categories of food, in appropriate frequencies and/or durations, providing the appropriate amount and type of nutrients, or the user is over or under consuming certain categories of food, leading to obesity or mal-nutrition. The results of the analysis may be stored in a subject specific data 434, which may be further processed to provide recommendations in supplementing and/or adjusting the user's food and/or beverage consumption habits.

Processes 300 and 400 presented in FIGS. 3 and 4 may be representative of example machine readable instructions for implementing the example system 100 of FIGS. 1 and 2. The machine readable instructions may comprise a program for execution by a processor such as the processor 122 shown in the example processor platform 600 discussed below in connection with FIG. 6. The program may be embodied in software stored on a non-transitory computer readable storage medium such as a CD-ROM, a floppy disk, a hard drive, a digital versatile disk (DVD), a Blu-ray disk, or a memory associated with the processor 122, but the entire program and/or parts thereof could alternatively be executed by a device other than the processor 122 and/or embodied in firmware or dedicated hardware. Further, although the example program is described with reference to the processes illustrated in FIGS. 3 and 4, many other methods of implementing the example system 100 and/or components thereof may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIGS. 3 and 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information).

The machine readable-instructions, when executed, may cause the example food and/or beverage analyzer 122/200 of FIGS. 1 and/or 2 to identify food chewed and/or beverage drank activities based on nasal bridge vibration data 112 collected from a user (e.g., the user 104 of FIG. 1). In the examples of FIGS. 3 and 4, the vibration data can be collected via sensor(s) 106 of the wearable device 102 of FIG. 1. The example instructions of FIGS. 3 and 4 can executed by the food and/or beverage analyzer 122/200 of FIGS. 1 and/or 2. The food and/or beverage analyzer 122 of FIGS. 1 and/or 2 can be located at the processor 114 of the wearable device 102, the processor 116 of the user device 118, and/or the cloud-based device 120. The instructions of FIGS. 3 and 4 can be executed in substantially real-time as the breathing data is generated and received by the food and/or beverage analyzer 122/200 or at some time after the vibration data is generated.

Figure 6:
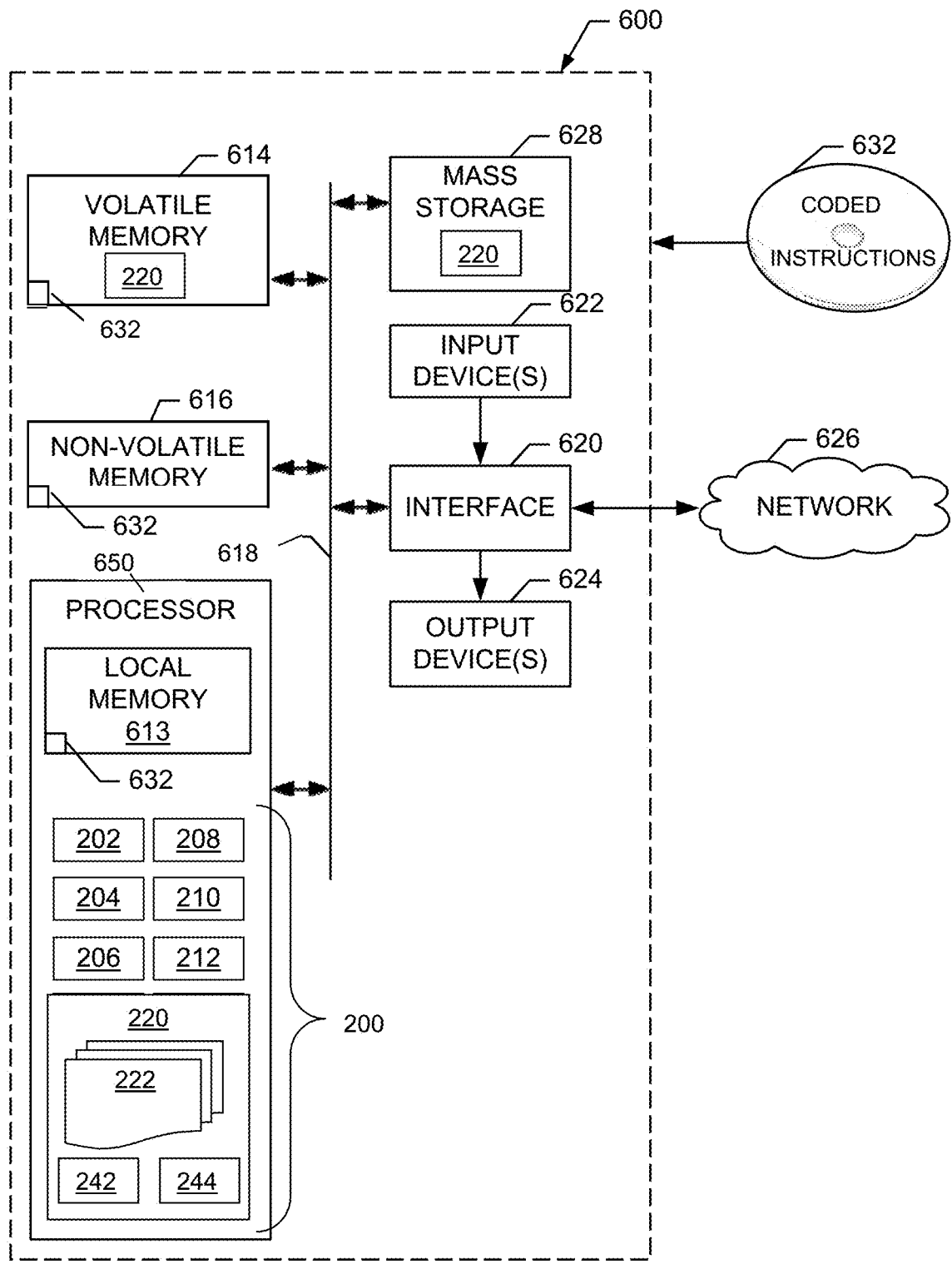
FIG. 6 illustrates an example computing platform that may be used to practice (aspects of) the present disclosure, according to various embodiments.

FIG. 6 is a block diagram of an example processor platform 600 capable of executing the instructions of FIGS. 3 and 4 to implement the example food & beverage analyzer 122/200 of FIGS. 1 and/or 2. The processor platform 600 can be, for example, a server, a personal computer, a mobile device (e.g., a cell phone, a smart phone, a tablet such as an iPad'), a personal digital assistant (PDA), an Internet appliance, wearable device such as eyeglasses, or any other type of computing device.

The processor platform 600 of the illustrated example includes a processor 650. The processor 650 of the illustrated example is hardware. For example, the processor 650 can be implemented by one or more integrated circuits, logic circuits, microprocessors or controllers from any desired family or manufacturer. The hardware processor 650 may be a semiconductor based (e.g., silicon based) device. In this example, the processor 650 implements the food and beverage analyzer a 122/200 and its components (e.g., the example breathing analyzer 202, the example artifacts analyzer 204, the example chewing analyzer 206, the example drinking analyzer 208, the example food classifier 210, the example beverage classifier 212 and so forth).

The processor 650 of the illustrated example may include a local memory 613 (e.g., a cache). The processor 650 of the illustrated example may be in communication with a main memory including a volatile memory 614 and a non-volatile memory 616 via a bus 618. The volatile memory 614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 616 may be implemented by flash memory and/or any other desired type of memory device. Access to the main memory 614, 616 is controlled by a memory controller. The database 220 of the food and beverage analyzer 122/200 may be implemented by the main memory 614, 616.

The processor platform 600 of the illustrated example may also include an interface circuit 620. The interface circuit 620 may be implemented by any type of interface standard, such as an Ethernet interface, a universal serial bus (USB), and/or a PCI express interface.

In the illustrated example, one or more input devices 622 may be connected to the interface circuit 620. The input device(s) 622 may permit a user to enter data and/or commands into the processor 650, e.g., inputting food chewing and/or beverage drinking signal profiles during training. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 624 may also be connected to the interface circuit 620 of the illustrated example. The output devices 624 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 620 of the illustrated example, thus, typically includes a graphics driver card, a graphics driver chip and/or a graphics driver processor.

The interface circuit 620 of the illustrated example may also include a communication device such as a transmitter, a receiver, a transceiver, a modem and/or network interface card to facilitate exchange of data with external machines (e.g., computing devices of any kind) via a network 626 (e.g., an Ethernet connection, a digital subscriber line (DSL), a telephone line, coaxial cable, a cellular telephone system, WiFi, NFC etc.).

The processor platform 600 of the illustrated example may also include one or more mass storage devices 628 for storing software and/or data. Examples of such mass storage devices 628 include floppy disk drives, hard drive disks, compact disk drives, Blu-ray disk drives, RAID systems, and digital versatile disk (DVD) drives.

The coded instructions of FIGS. 3 and 4, as well as instructions of operating system and/or other applications 632 may be stored in the mass storage device 628, in the volatile memory 614, in the non-volatile memory 616, and/or on a removable tangible computer readable storage medium such as a CD or DVD.

From the foregoing, it will be appreciated that methods, systems, and apparatus have been disclosed to identify food/chewing and/or beverage/drinking by a user/subject. Disclosed examples analyze vibration signal data. The vibration signal data may be nasal bridge vibration signal data collected from a user wearing a wearable device such as eyeglasses including piezoelectric sensors to detect nasal bridge vibrations. In some examples, the analysis may be performed at the wearable device, at a user device such as a smartphone, and/or via a cloud-based device. Disclosed examples extract features of chewing and/or drinking activities from the vibration data. Other disclosed examples use machine learning algorithms to identify additional features useful for identifying chewing and/or drinking activities. Disclosed examples used the extracted features to identify chewing and/or drinking activities. Disclosed examples used the identified chewing and/or drinking activities to identify categories of food and/or beverages consumed.

The following is a non-exclusive list of examples disclosed herein. Other examples may be included above. In addition, any of the examples disclosed herein can be considered in whole or in part, and/or modified in other ways.

Example 1 may be a device comprising: one or more sensors positioned to sense vibrations from a nasal bridge of a user wearing the device, and generate vibration signal data representative of the sensed vibrations, responsive to selective activities of the user; and at least one of a chewing analyzer or a drinking analyzer. The chewing analyzer is to receive and process the vibration signal data to attempt to extract from the vibration signal data a first plurality of features associated with chewing activities; and the drinking analyzer is to receive and process the vibration signal data to attempt to extract from the vibration signal data a second plurality of features associated with drinking activities. On extraction, the extracted first plurality of features are used to determine a category of food the user was chewing, and the extracted second plurality of features are used to determine a category of beverage the user was drinking.

Example 2 may be example 1, wherein to attempt to extract from the vibration signal data a first plurality of features associated with chewing activities, the chewing analyzer is to analyze the vibration signal data for an average amount of energy present between a frequency band of about 0-22 kHz over a time period.

Example 3 may be example 1, wherein to attempt to extract from the vibration signal data a first plurality of features associated with chewing activities, the chewing analyzer is to analyze the vibration signal data for a duration ratio of a first duration of a first time period with energy above an energy threshold, and a second duration of a second time period, immediately following the first time period, with energy below the energy threshold.

Example 4 may be example 1, wherein to attempt to extract from the vibration signal data a first plurality of features associated with chewing activities, the chewing analyzer is to analyze the vibration signal data for a number energy peaks above a frequency threshold between two time periods with energy below an energy threshold.

Example 5 may be example 1, wherein to attempt to extract from the vibration signal data a first plurality of features associated with chewing activities, the chewing analyzer is to analyze the vibration signal data for a weighted average frequency for a time period.

Example 6 may be example 1, wherein to attempt to extract from the vibration signal data a second plurality of features associated with drinking activities, the drinking analyzer is to analyze the vibration signal data for a size of a duration between two successive energy bursts below about 5 kHz.

Example 7 may be example 1, wherein to attempt to extract from the vibration signal data a second plurality of features associated with drinking activities, the drinking analyzer is to analyze the vibration signal data for an integrated amount of energy over a time period.

Example 8 may be example 1, wherein to attempt to extract from the vibration signal data a second plurality of features associated with drinking activities, the drinking analyzer is to analyze the vibration signal data for a number of swallowing incidents.

Example 9 may be example 1, further comprising at least a selected one of a food classifier or a beverage classifier; wherein the food classifier is coupled to the chewing analyzer to receive and process the extracted first plurality of features associated with chewing activities to determine the category of food the user was chewing; and wherein the beverage classifier is coupled to the drinking analyzer to receive and process the extracted second plurality of features associated with drinking activities to determine the category of beverage the user was drinking.

Example 10 may be example 9, wherein at least one of the chewing analyzer, the drinking analyzer, the food classifier or the beverage classifier performs the extraction of the first plurality of features associated with chewing activities, the extraction of the second plurality of features associated with drinking activities, the determination of a category of food or the determination of a category of beverage, based at least in part on one or more personalized chewing and drinking models of the user.

Example 11 may be example 1, further comprising a breathing analyzer to receive and process the vibration signal data to determine whether the vibration signal data are representative of breathing of the user; wherein the chewing analyzer is coupled to the breathing analyzer, and performs the processing of the vibration signal data to attempt to extract from the vibration signal data the first plurality of features associated with chewing activities, based at least in part on determination that the vibration signal data are not representative of breathing of the user; and wherein the drinking analyzer is coupled to the breathing analyzer, and performs the processing of the vibration signal data to attempt to extract from the vibration signal data the second plurality of features associated with drinking activities, based at least in part on determination that the vibration signal data are not representative of breathing of the user.

Example 12 may be example 1, further comprising an artifact analyzer to receive and process the vibration signal data to determine whether the vibration signal data are representative of one or more artifacts of the user; wherein the chewing analyzer is coupled to the artifact analyzer, and perform the processing of the vibration signal data to attempt to extract from the vibration signal data the first plurality of features associated with chewing activities, based at least in part on determination that the vibration signal data are not representative of one or more artifacts of the user; and wherein the drinking analyzer is coupled to the artifact analyzer, and perform the processing of the vibration signal data to attempt to extract from the vibration signal data the second plurality of features associated with drinking activities, based at least in part on determination that the vibration signal data are not representative of one or more artifacts of the user.

Example 13 may be example 12, wherein one or more artifacts comprise one or more of coughing, scratching forehead, sneezing or yawning.

Example 14 may be any one of examples 1-12, wherein the device is an eyewear having a frame with a nose bridge and a plurality of bridge arms, and the one or more sensors are proximally disposed at the bridge arms.

Example 15 may be a method comprising: sensing with a plurality of sensors vibrations at a nose bridge of a user, and generating sensor data representative of the vibrations sensed; analyzing the sensor data to determine whether the sensor data represents breathing of the user; and on determining that the sensor data do not represent breathing of the user, determining chewing activities the user was engaged in, or drinking activities the user was engaged in, based at least in part on the sensor data and one or more personalized chewing or drinking models of the user.

Example 16 may be example 15, further comprising filtering artifacts from the sensor data prior to determining the chewing activities the user was engaged in, or the drinking activities the user was engaged in.

Example 17 may be example 15, wherein determining chewing activities the user was engaged in, or drinking activities the user was engaged in comprises processing the sensor data to attempt to extract from the sensor data a first plurality of features associated with chewing activities or a second plurality of features associated with drinking activities, then determining the chewing activities the user was engaged in, or the drinking activities the user was engaged in, based at least in part on the extracted first or second plurality of features, and the one or more personalized chewing or drinking models of the user.

Example 18 may be example 17, further comprising creating the one or more personalized chewing and drinking models of the user.

Example 19 may be at least one computer-readable medium (CRM) having instructions stored therein to cause an eyewear, in response to execution of the instructions by a processor of the eyewear, to operate at least one of a chewing analyzer or a drinking analyzer; wherein the chewing analyzer is to receive and process vibration signal data to attempt to extract from the vibration signal data a first plurality of features associated with chewing activities; wherein the drinking analyzer is to receive and process the vibration signal data to attempt to extract from the vibration signal data a second plurality of features associated with drinking activities; and wherein the vibration signal data are provided by one or more sensors of the eyewear positioned to sense vibrations from a nasal bridge of a user wearing the eyewear, and are generated representative of the sensed vibrations, responsive to selective activities of the user.

Example 20 may be example 19, wherein the eyewear are further caused to operate at least a selected one of a food classifier or a beverage classifier; wherein the food classifier is to receive and process the extracted first plurality of features associated with chewing activities to determine a category of food the user was chewing; and wherein the beverage classifier is to receive and process the extracted second plurality of features associated with drinking activities to determine a category of beverage the user was drinking.

Example 21 may be example 20, wherein at least one of the chewing analyzer, the drinking analyzer, the food classifier or the beverage classifier performs the extraction of the first plurality of features associated with chewing activities, the extraction of the second plurality of features associated with drinking activities, the determination of a category of food or the determination of a category of beverage, based at least in part on one or more personalized chewing and drinking models of the user.

Example 22 may be example 19, wherein the eyewear are further caused to operate a breathing analyzer to receive and process the vibration signal data to determine whether the vibration signal data are representative of breathing of the user; wherein the chewing analyzer is to perform the processing of the vibration signal data to attempt to extract from the vibration signal data the first plurality of features associated with chewing activities, based at least in part on determination that the vibration signal data are not representative of breathing of the user; and wherein the drinking analyzer is to perform the processing of the vibration signal data to attempt to extract from the vibration signal data the second plurality of features associated with drinking activities, based at least in part on determination that the vibration signal data are not representative of breathing of the user.

Example 23 may be example 19, wherein the eyewear are further caused to operate an artifact analyzer to receive and process the vibration signal data to determine whether the vibration signal data are representative of one or more artifacts of the user; wherein the chewing analyzer is to perform the processing of the vibration signal data to attempt to extract from the vibration signal data the first plurality of features associated with chewing activities, based at least in part on determination that the vibration signal data are not representative of one or more artifacts of the user; and wherein the drinking analyzer is to perform the processing of the vibration signal data to attempt to extract from the vibration signal data the second plurality of features associated with drinking activities, based at least in part on determination that the vibration signal data are not representative of one or more artifacts of the user.

Example 24 may be example 19, wherein to attempt to extract from the vibration signal data a first plurality of features associated with chewing activities, the chewing analyzer is to analyze the vibration signal data for at least one of: an average amount of energy present between a frequency band of about 0-22 kHz over a time period, a duration ratio of a first duration of a first time period with energy above an energy threshold, and a second duration of a second time period, immediately following the first time period, with energy below the energy threshold, a number energy peaks above a frequency threshold between two time periods with energy below an energy threshold, or a weighted average frequency for a time period.

Example 25 may be any one of examples 19-24, wherein to attempt to extract from the vibration signal data a second plurality of features associated with drinking activities, the drinking analyzer is to analyze the vibration signal data for at least one of: a size of a duration between two successive energy burst below about 5 kHz, an integrated amount of energy over a time period, or a number of swallowing incidents.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A device comprising:
   one or more sensors positioned to sense vibrations from a nasal bridge of a user wearing the device, and generate vibration signal data representative of the sensed vibrations, responsive to selective activities of the user; and
   a chewing analyzer to receive and process the vibration signal data to attempt to extract from the vibration signal data a first plurality of features associated with chewing activities;
   wherein on extraction, the extracted first plurality of features are used to determine a category of food the user was chewing;
   wherein to attempt to extract from the vibration signal data the first plurality of features associated with chewing activities, the chewing analyzer is to analyze the vibration signal data for a number of energy peaks above a frequency threshold between two time periods with energy below an energy threshold, or to analyze the vibration signal data for a weighted average frequency for a time period.

2. The device of claim 1, wherein to attempt to extract from the vibration signal data a first plurality of features associated with chewing activities, the chewing analyzer is to analyze the vibration signal data for an average amount of energy present between a frequency band of 0-22 kHz over a time period.

3. The device of claim 1, wherein to attempt to extract from the vibration signal data a first plurality of features associated with chewing activities, the chewing analyzer is to analyze the vibration signal data for a duration ratio of a first duration of a first time period with energy above an energy threshold, and a second duration of a second time period, immediately following the first time period, with energy below the energy threshold.

4. The device of claim 1, further comprising a drinking analyzer to receive and process the vibration signal data to attempt to extract from the vibration signal data a second plurality of features associated with drinking activities;
   wherein to attempt to extract from the vibration signal data a second plurality of features associated with drinking activities, the drinking analyzer is to analyze the vibration signal data for a size of a duration between two successive energy bursts below 5 kHz.

5. The device of claim 4, wherein to attempt to extract from the vibration signal data a second plurality of features associated with drinking activities, the drinking analyzer is to analyze the vibration signal data for an integrated amount of energy over a time period.

6. The device of claim 4, wherein to attempt to extract from the vibration signal data a second plurality of features associated with drinking activities, the drinking analyzer is to analyze the vibration signal data for a number of swallowing incidents.

7. The device of claim 1, further comprising
   a food classifier coupled to the chewing analyzer to receive and process the extracted first plurality of features associated with chewing activities to determine the category of food the user was chewing.

8. The device of claim 7, wherein at least one of the chewing analyzer or the food classifier performs the extraction of the first plurality of features associated with chewing activities, or the determination of a category of food, based at least in part on one or more personalized chewing and drinking models of the user.

9. The device of claim 1, further comprising a breathing analyzer to receive and process the vibration signal data to determine whether the vibration signal data are representative of breathing of the user;
   wherein the chewing analyzer is coupled to the breathing analyzer, and performs the processing of the vibration signal data to attempt to extract from the vibration signal data the first plurality of features associated with chewing activities, based at least in part on determination that the vibration signal data are not representative of breathing of the user.

10. The device of claim 1, further comprising an artifact analyzer to receive and process the vibration signal data to determine whether the vibration signal data are representative of one or more artifacts of the user;
    wherein the chewing analyzer is coupled to the artifact analyzer, and perform the processing of the vibration signal data to attempt to extract from the vibration signal data the first plurality of features associated with chewing activities, based at least in part on determination that the vibration signal data are not representative of one or more artifacts of the user.

11. The device of claim 10, wherein one or more artifacts comprise one or more of coughing, scratching forehead, sneezing or yawning.

12. The device of claim 1, wherein the device is an eyewear having a frame with a nose bridge and a plurality of bridge arms, and the one or more sensors are proximally disposed at the bridge arms.

13. A method comprising:
    sensing with a plurality of sensors vibrations at a nose bridge of a user, and generating sensor data representative of the vibrations sensed;
    analyzing the sensor data to determine whether the sensor data represents breathing of the user; and
    on determining that the sensor data do not represent breathing of the user, extracting from the vibration signal data a first plurality of features to determine chewing activities the user was engaged in, based at least in part on one or more personalized chewing models of the user;
    wherein extracting from the vibration signal data the first plurality of features associated with chewing activities comprises analyzing the vibration signal data for a number of energy peaks above a frequency threshold between two time periods with energy below an energy threshold, or analyzing the vibration signal data for a weighted average frequency for a time period.

14. The method of claim 13, further comprising filtering artifacts from the sensor data prior to determining the chewing activities the user was engaged in, or drinking activities the user was engaged in.

15. The method of claim 13, further comprising extracting from the sensor data a second plurality of features associated with drinking activities to determine drinking activities the user was engaged in, based at least in part on one or more personalized drinking models of the user.

16. The method of claim 15, further comprising creating the one or more personalized chewing and drinking models of the user.

17. At least one non-transitory computer-readable medium (CRM) having instructions stored therein to cause an eyewear, in response to execution of the instructions by a processor of the eyewear, to operate a chewing analyzer to receive and process vibration signal data to attempt to extract from the vibration signal data a first plurality of features associated with chewing activities;

wherein the vibration signal data are provided by one or more sensors of the eyewear positioned to sense vibrations from a nasal bridge of a user wearing the eyewear, and are generated representative of the sensed vibrations, responsive to selective activities of the user; and wherein to attempt to extract from the vibration signal data the first plurality of features associated with chewing activities, the chewing analyzer is to analyze the vibration signal data for at least one of:

an average amount of energy present between a frequency band of 0-22 kHz over a time period, or a duration ratio of a first duration of a first time period with energy above an energy threshold, and a second duration of a second time period, immediately following the first time period, with energy below the energy threshold.

18. The non-transitory CRM of claim 17, wherein the eyewear is further caused to operate a food classifier to receive and process the extracted first plurality of features associated with chewing activities to determine a category of food the user was chewing.

19. The non-transitory CRM of claim 18, wherein at least one of the chewing analyzer or the food classifier performs the extraction of the first plurality of features associated with chewing activities, or the determination of a category of food or the determination of a category of beverage, based at least in part on one or more personalized chewing models of the user.

20. The non-transitory CRM of claim 19, wherein the eyewear is further caused to operate a breathing analyzer to receive and process the vibration signal data to determine whether the vibration signal data are representative of breathing of the user;

wherein the chewing analyzer is to perform the processing of the vibration signal data to attempt to extract from the vibration signal data the first plurality of features associated with chewing activities, based at least in part on determination that the vibration signal data are not representative of breathing of the user.

21. The non-transitory CRM of claim 19, wherein the eyewear is further caused to operate an artifact analyzer to receive and process the vibration signal data to determine whether the vibration signal data are representative of one or more artifacts of the user;

wherein the chewing analyzer is to perform the processing of the vibration signal data to attempt to extract from the vibration signal data the first plurality of features associated with chewing activities, based at least in part on determination that the vibration signal data are not representative of one or more artifacts of the user.

22. The non-transitory CRM of claim 17, wherein to attempt to extract from the vibration signal data a first plurality of features associated with chewing activities, the chewing analyzer is to further analyze the vibration signal data for:

a number of energy peaks above a frequency threshold between two time periods with energy below an energy threshold, or a weighted average frequency for a time period.

23. The non-transitory CRM of claim 17, wherein the eyewear is further caused to operate a drinking analyzer to receive and process the vibration signal data to attempt to extract from the vibration signal data a second plurality of features associated with drinking activities;

wherein to attempt to extract from the vibration signal data a second plurality of features associated with drinking activities, the drinking analyzer is to analyze the vibration signal data for at least one of:

a size of a duration between two successive energy burst below 5 kHz, an integrated amount of energy over a time period, or a number of swallowing incidents.

* * * * *